(12) United States Patent
Dodge et al.

(10) Patent No.: US 7,462,647 B2
(45) Date of Patent: Dec. 9, 2008

(54) PENTALFLUOROALKANESULFINYL NAPHTHALENES AND RELATED ESTROGEN RECEPTOR MODULATORS

(75) Inventors: Jeffrey Alan Dodge, Indianapolis, IN (US); Norman Earle Hughes, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 642 days.

(21) Appl. No.: 10/557,730

(22) PCT Filed: May 27, 2004

(86) PCT No.: PCT/US2004/014534
§ 371 (c)(1), (2), (4) Date: Nov. 18, 2005

(87) PCT Pub. No.: WO2005/000834
PCT Pub. Date: Jan. 6, 2005

(65) Prior Publication Data
US 2007/0054956 A1 Mar. 8, 2007

Related U.S. Application Data

(60) Provisional application No. 60/477,272, filed on Jun. 10, 2003.

(51) Int. Cl.
*A61K 31/10* (2006.01)
*C07C 317/06* (2006.01)

(52) U.S. Cl. .................. 514/708; 568/27
(58) Field of Classification Search ............ 568/27; 514/708
See application file for complete search history.

(56) References Cited
U.S. PATENT DOCUMENTS
5,807,899 A 9/1998 Bohlmann et al.

FOREIGN PATENT DOCUMENTS
| EP | 0 747 377 | 12/1996 |
| EP | 0 902 025 | 3/1999 |
| EP | 0 905 132 | 3/1999 |
| EP | 0902025 A2 * | 3/1999 |
| EP | 1 241 158 | 9/2002 |
| WO | WO 95/10513 | 4/1995 |
| WO | WO 01/27127 | 4/2001 |

OTHER PUBLICATIONS

Jin, et al., "Antiestrogenic Activity of Two 11β-estradiol Derivatives on MCF-7 Breast Cancer Cells," *Steroids*, vol. 60, pp. 512-518 (1995).
Robertson, "Faslodex (ICI 182, 780) a novel estrogen receptor downregulator—future possibilities in breast cancer," *Journal of Steroid Biochemistry & Molecular Biology*, vol. 79, pp. 209-212 (2001).
O'Regan, et al, "Tamoxifen to Raloxifene and Beyond," *Seminars in Oncology*, vol. 28, No. 3, pp. 260-273 (2001).

* cited by examiner

*Primary Examiner*—Rei-Tsang Shiao
*Assistant Examiner*—Janet L Coppins
(74) *Attorney, Agent, or Firm*—John C. Demeter

(57) ABSTRACT

The present invention provides a compound of the formula (I) wherein R is —H, or —$C_1$-$C_4$ alkyl; $R^1$ is —H, —OH, —O($C_1$-$C_4$ alkyl), —$SO_2$($C_1$-$C_4$ alkyl), or halo; X is —O—, —$CH_2$—, or —C(O)—; $X^1$ is —O— or —$NR^2$—; $R^2$ is —H or —$CH_3$; Y is —S—, —$CH_2CH_2$—, or —HC=CH—; m is 0, 1, 2, or 3; and n is 0 or 1; or a pharmaceutically acceptable salt thereof; pharmaceutical compositions thereof; and methods for inhibiting a disease associated with an aberrant physiological response to endogenous estrogen.

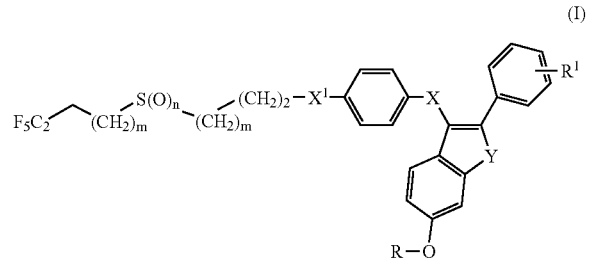

4 Claims, No Drawings

PENTALFLUOROALKANESULFINYL NAPHTHALENES AND RELATED ESTROGEN RECEPTOR MODULATORS

This application claims the benefit under 35 U.S.C. § 120 of International Application No. PCT/US2004/014534, filed May 27, 2004, which claims the benefit under 35 U.S.C. § 119(e) of U.S. Serial No. 60/477,272, filed Jun. 10.2003.

BACKGROUND OF THE INVENTION

The present invention relates to pentafluoroalkane sulfinyl naphthalenes and related compounds, compositions containing those compounds, their use as estrogen receptor modulators, and their use in inhibiting breast and uterine carcinoma. Breast carcinoma or cancer is a major medical problem for women beginning in the third decade of life and continuing throughout senescence. It is currently estimated that in the United States women have a one in eight chance of developing the disease in their lifetime (by the age of eighty), whereas one in twenty-eight women have a lifetime risk of dying from breast cancer (Harris et. al., Ed. Diseases of the Breast, 1996: pp. 159-168). Carcinoma of the breast is the third most common cancer, and the most common cancer in women. It is a major cause of mortality in women, as well as a cause of disability, psychological trauma, and economic loss. Breast carcinoma is the second most common cause of cancer death in women in the United States, and for women between the ages of 15 and 54, the leading cause of cancer-related death (Forbes, Seminars in Oncology, vol. 24(1), Suppl 1, 1997: pp. S1-20-S1-35). Indirect effects of the disease also contribute to the mortality from breast cancer including consequences of advanced disease, such as metastases to the bone or brain. Complications arising from bone marrow suppression, radiation fibrosis and neutropenic sepsis, collateral effects from therapeutic interventions, such as surgery, radiation, chemotherapy, or bone marrow transplantation—also contribute to the morbidity and mortality from this disease.

The epidemiology of this disease, although the subject of intense investigation, is still poorly understood. There appears to be a substantial genetic component which predisposes some women to contract the disease. Yet it is not clear whether this genetic component is causative or permissive to the disease, or only predictive of the disease process. Although it has been known for a long time that breast carcinoma tends to occur more frequently in some families, such analysis is not always predictive of disease occurrence in other family members and is of little value for prediction of its prevalence in the general population. It is currently estimated that only 5% of all breast cancers result from a genetic predisposition (Harris et. al., Ed. Disease of the Breast, 1996: pp. 159-168).

Extensive clinical and pharmacological investigation has been conducted in the attempt to elucidate the relationship between the hormone estrogen, and the cause and maintenance of breast carcinoma. Risk factors for the disease are principally related to the duration of a woman's cumulative estrogen exposure and include: age at menarche, parity, age at the time of the first full-term pregnancy, and menopause. Although much is known about the relationship of estrogen in the maintenance of the disease and the importance of estrogen dependence with respect to endocrine treatment of the disease, there is considerable controversy over the role of estrogen in the pathogenesis of this disease, i.e., whether estrogen is a causative agent (initiator), or an obligatory co-factor (promotor) in the process of carcinogenesis.

Estrogen, which includes 17-beta-estradiol, estrone, and their active metabolites, is a major sex-related hormone in women, but additionally, it appears to be an important homeostatic hormone in both men and women throughout their adult life. All humans have some level of endogenous estrogen. Yet the vast majority of people do not develop breast carcinoma, supporting a position that estrogen, per se, is not an initiator of carcinogenesis, such as is the case with a chemical or environmental carcinogen. Additionally, women, as they go through menopause with the consequent loss of endogenous ovarian estrogen production, do not experience a commensurate reduction in their risk of contracting this disease. In fact, apart from a personal history of breast cancer, age is the single greatest risk factor for developing this disease. Breast cancer is rare in women younger than age 20, but this risk increases rapidly with age. When compared with a 20-year-old woman's risk of developing breast cancer, a woman age 40 to 49 has a 40-fold increase in risk, a woman age 50 to 59 a 60-fold increase, and a woman over the age of 60 has a risk 90-fold higher than that of her younger counterpart (Forbes, Seminars in Oncology, vol. 24(1), Suppl 1, 1997: pp. S1-20-S1-35).

Theories and evidence regarding the role of estrogen in the pathogenesis of this disease are complex. Experimental models of mammary carcinoma in rats require administration of a carcinogen for tumor induction (tumorigenesis), whereas estrogen behaves as a promoter (rather than an initiator) of this process. Ovariectomy, in these animal models, will interfere with this process of chemically-induced carcinogenesis. In humans, however, the timing of the carcinogenic event is unknown. What is known is that women who undergo premature menopause or medical or surgical oophorectomy before the age of 40, will have an approximately 50% reduction in breast cancer risk compared with women undergoing natural menopause at age 50 (Harris, et. al., Ed. Diseases of the Breast, 1996: pp. 159-168). It is logical, therefore, that approaches for the prevention of breast cancer would target the reduction in lifetime estrogen exposure. This can be accomplished by pharmacologically-induced estrogen deprivation, through the administration of an agent which would block the production and/or action of estrogen anywhere along the hypothalamic-pituitary-gonadal axis. It is nevertheless problematic to extrapolate the probable success of preventing breast carcinoma, de novo or otherwise, with agents of this nature.

In contrast to the complex role of estrogen in the pathogenesis of this disease, and despite a continually evolving body of data, considerable advances have been made in our understanding of the effects of estrogen in the setting of established breast carcinoma. Estrogen is a growth factor to most breast carcinoma cells in the early stages of the disease. The rapidly dividing cells are sensitive to its effects through the estrogen receptor. It has also been established, although not well understood that, at some point during the course of this disease process, transformed (cancer) cells often lose their sensitivity to the promoting effects of estrogen. Eventually, a majority of carcinoma cells become independent of estrogen for growth and lose their responsiveness to hormonally based therapy, which broadly includes: the GNRH agonists, tamoxifen, progestins, and androgens.

Enormous benefit in the treatment of breast cancer has been achieved with the advent and widespread use of hormonally based therapeutic interventions. The most extensively used endocrine therapy is tamoxifen. The five-year survival rate for women with breast carcinoma has been dramatically improved with this therapy; however, no additional benefit or survival advantage is achieved by continuing therapy for more than five years. In fact, data indicate a decrease in disease-free survival as well as overall survival, with greater than five years tamoxifen use (NSABP B-14 Trial; Fisher et al. Five Versus More Than Five Years of Tamoxifen Therapy for Breast Cancer Patients With Negative Lymph Nodes and Estrogen Receptor-Positive Tumors, *J Natl Canc Inst*, vol. 88)(21): pp. 1529-1542, 1996). Unfortunately tamoxifen is also associated with significant adverse effects such as: a significantly increased incidence of venous thromboembolism, substantially increased incidence of vasomotor symptoms or hot flashes (in the range of 16-67%), cataract formation, and DNA-adduct formation which, although not clinically confirmed, still raises concerns about the potential for hepatocellular carcinoma (observed experimentally in animal models). The most serious event, however, is tamoxifen's estrogenic effect in the uterus which causes endometrial hyperplasia and a substantial increase in the incidence-of endometrial carcinomas (a three to four-fold increase in risk after five years tamoxifen-administration) (Goldhirsch et. al., Endocrinie Therapies of Breast Cancer, Sem in One, vol. 23(4), pp. 494-505, 1996). For this reason and the lack of improvement in survival advantage with long-term tamoxifen use, tamoxifen therapy of longer than five years is now contraindicated.

Data suggest that with long-term tamoxifen exposure, breast tumor cells undergo alterations that cause them to develop resistance to its antiestrogenic effects, and alternatively respond to its estrogenic properties (Santen, Editorial: Long Term Tamoxifen Therapy: Can an Antagonist become an Agonist?, J Clin Endo & Metab, vol. 81(6), pp. 2027-2029, 1996). Changes in any step in the estrogen receptor signaling pathway may be responsible for the mechanism of development of resistance to tamoxifen therapy, some of which do not cause cross-resistance to other hormonal therapies and some of which do result in complete unresponsiveness to endocrine therapy of any kind. One mechanism for tamoxifen resistance has been attributed to the gradual evolution of the carcinoma cells from estrogen dependence to estrogen independence (estrogen receptor positive cells become estrogen receptor negative). Thus, even with the most advanced available combinations of treatment modalities, (surgery, radiation, and/or chemotherapy), the long-term prognosis for patients is poor, especially when metastatic disease is present. Clearly, there is a great need for improved therapies and, perhaps most important, a critical need for the prevention of the disease in the first instance (de novo, or primary prevention).

BRIEF SUMMARY OF THE INVENTION

The present invention provides a compound of the formula

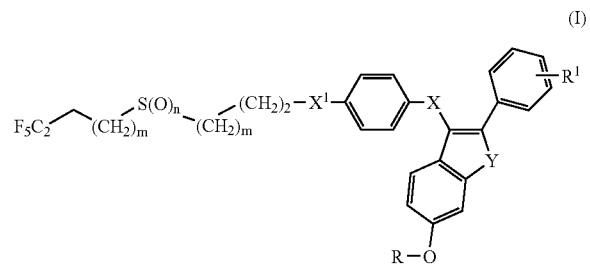

(I)

wherein
R is —H, or —$C_1$-$C_4$ alkyl;

$R^1$ is —H, —OH, —O($C_1$-$C_4$ alkyl), —$SO_2$($C_1$-$C_4$ alkyl), or halo;
X is —O—, —$CH_2$—, or —C(O)—;
$X^1$ is —O— or —$NR^2$—;
$R^2$ is —H or —$CH_3$;
Y is —S—, —$CH_2CH_2$—, or —HC═CH—;
m is 0, 1, 2, or 3; and
n is 0 or 1;

or a pharmaceutically acceptable salt thereof.

In a second embodiment, the present invention provides a pharmaceutical composition comprising a therapeutically effective amount of a compound of formula (I) and a pharmaceutically acceptable carrier.

In an alternative embodiment of the medical method of the present invention, the compounds of the present invention are employed in the treatment or prevention of disease conditions associated with an aberrant physiological response to endogenous estrogen including breast cancer and endometrial cancer.

In a still further embodiment, the invention relates to chemical intermediates used in synthesizing the compounds of Formula (I).

DETAILED DESCRIPTION OF THE INVENTION

General terms used in the description of compounds herein described bear their usual meanings. For example, "$C_1$-$C_6$ alkyl" refers to straight, branched, or cyclic aliphatic chains of 1 to 6 carbon atoms including moieties such as methyl, ethyl, propyl, isopropyl, butyl, n-butyl, pentyl, isopentyl, hexyl, isohexyl, cyclohexyl and the like. Likewise, "$C_1$-$C_4$ alkyl" refers to straight, branched, or cyclic aliphatic chains of 1 to 4 carbon atoms including moieties such as methyl, ethyl, propyl, isopropyl, butyl, n-butyl, cyclopropyl, and the like. Similarly, the term "$C_1$-$C_4$alkoxy" represents a $C_1$-$C_4$ alkyl group attached through an oxygen molecule and include moieties such as, for example, methoxy, ethoxy, n-propoxy, isopropoxy, and the like.

The term "halo" refers to bromo, chloro, fluoro and iodo.

The designation " ▬ " refers to a bond that protrudes forward out of the plane of the page.

The designation " ''''' " refers to a bond that protrudes backward out of the plane of the page.

The designation " ∼ " refers to a bond wherein the stereochemistry is not defined.

Preferred Compounds (Embodiments) of the Invention

Certain compounds of the invention are particularly interesting and are preferred.

The following listing sets out several groups of preferred compounds. It will be understood that each of the listings may be combined with other listings to create additional groups of preferred compounds.

a) m is 2;
b) n is 1;
c) R is —H;
d) $R^1$ is —OH, fluoro, chloro, or methoxy;
e) $R^1$ is —OH or methoxy;
f) $R^1$ is —OH, fluoro, chloro, or methoxy, and is at the para-position of the phenyl ring to which it is attached;

g) R¹ is —OH or methoxy, and is at the para-position of the phenyl ring to which it is attached;

h) X is —O—;

i) X¹ is —O—;

j) Y is —HC=CH—;

k) Y is —S— l) the compound of formula I is the hydrochloride salt.

Although the free-base or acid forms of formula I compounds can be used in the methods of the present invention, it is preferred to prepare and use a pharmaceutically acceptable salt form. Thus, the compounds used in the methods of this invention form pharmaceutically acceptable acid or base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

Typical bases used to form pharmaceutically acceptable addition salts would be inorganic bases, such as, sodium hydroxide, potassium hydroxide; alkali carbonates or bicarbonates, calcium carbonate, magnesium carbonate, and the like. Additionally, organic bases may be utilized to form addition salts, e.g., alkyl amines, such as, triethylamine, dimethylamine, i-propylamine, and the like.

The pharmaceutically acceptable acid or base addition salts are typically formed by reacting a compound of formula I with an equimolar or excess amount of acid or base. The reactants are generally combined in a mutual solvent such as diethyl ether or ethyl acetate. The salt normally precipitates out of solution within about one hour to 10 days and can be isolated by filtration or the solvent can be stripped off by conventional means.

Specific examples of compounds contemplated as falling within the scope of the present invention include, but are not limited to the following compounds and their pharmaceutically acceptable salts:

6-(4-Methoxy-phenyl)-5-{4-[4-(4,4,5,5,5-pentafluoro-pentane-sulfinyl)-butoxy]-phenoxy}-naphthalen-2-ol;

6-(4-Methoxy-phenyl)-5-{4-[4-(4,4,5,5,5-pentafluoro-pentylsulfanyl)-butoxy]-phenoxy}-naphthalen-2-ol;

6-(4-Hydroxy-phenyl)-5-{4-[4-(4,4,5,5,5-pentafluoro-pentane-sulfinyl)-butoxy]-phenoxy}-naphthalen-2-ol;

6-(4-Hydroxy-phenyl)-5-{4-[4-(4,4,5,5,5-pentafluoro-pentylsulfanyl)-butoxy]-phenoxy}-naphthalen-2-ol;

6-(4-Methoxy-phenyl)-5-{4-[4-(4,4,5,5,5-pentafluoro-pentane-sulfinyl)-butoxy]-phenoxy}-benzothiophen-2-ol;

6-(4-Methoxy-phenyl)-5-{4-[4-(4,4,5,5,5-pentafluoro-pentylsulfanyl)-butoxy]-phenoxy}-benzothiophen-2-ol;

6-(4-Hydroxy-phenyl)-5-{4-[4-(4,4,5,5,5-pentafluoro-pentane-sulfinyl)-butoxy]-phenoxy}-benzothiophen-2-ol; and 6-(4-Hydroxy-phenyl)-5-{4-[4-(4,4,5,5,5-pentafluoro-pentylsulfanyl)-butoxy]-phenoxy}-benzothiophen-2-ol.

Synthesis

The compounds of formula (I) can be prepared by utilizing procedures and techniques well known and appreciated by one of ordinary skill in the art. A general synthetic scheme for preparing compounds of formula (I) is set forth in Scheme A, wherein all substituents, unless otherwise indicated, are previously defined

SCHEME A

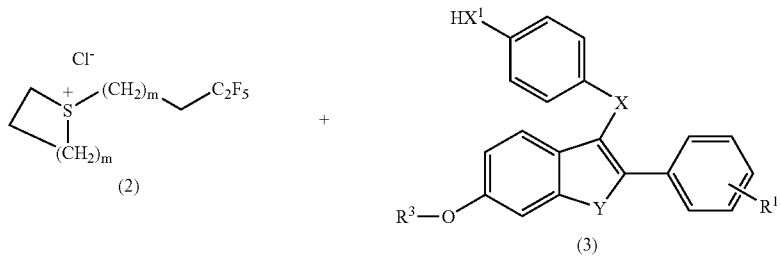

step 1

-continued

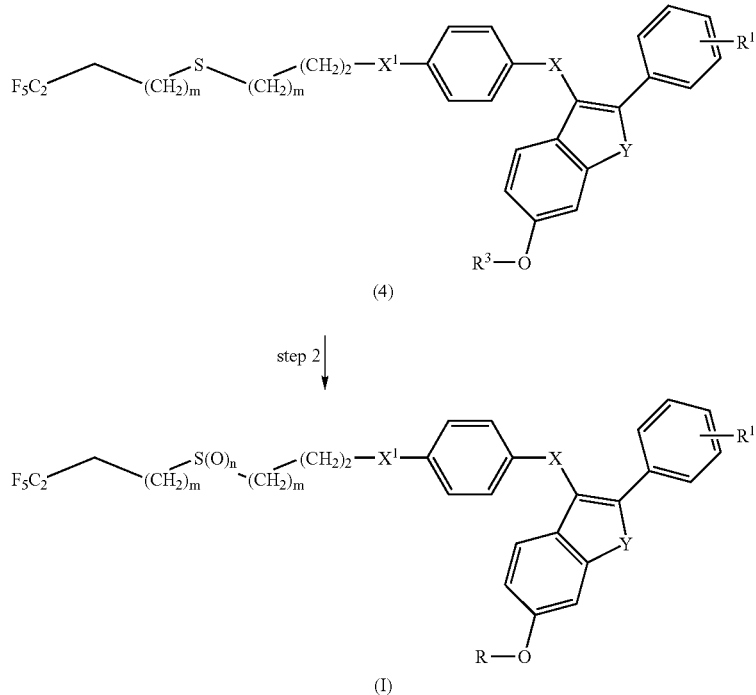

In Scheme A, $R^3$ is a phenolic protecting groups of the type taught by T. Greene, et al. in Chapter 3 of "Protective Groups in Organic Synthesis," Second Edition, John Wiley & Sons, Inc., New York, 1991, pp. 143-170. The preferred protecting groups are alkyl or benzyl, with benzyl being particularly preferred.

In Scheme A, step 1, pentafluoro-alkylsulfanyl compound of formula (4) is prepared by alkylating a substituted phenolic compound of formula (3) with a pentafluoro-alkyl-tetrahydrothiophenium chloride of formula (2).

For example, a substituted phenolic compound of formula (3) is dissolved in a suitable aprotic organic solvent such as tetrahydrofuran (THF), the solution is cooled to about 0° C., and a suitable amine base, such as sodium bis(trimethylsilyl) amide, is then added. Next, a pentafluoro-alkyl-tetrahydrothiophenium chloride of formula (2) is added in equimolar amounts compared to the amine base and the solution is allowed to warm to room temperature. The solution is then heated to a temperature ranging from about 50° C. to about 70° C. and stirred for a period of time ranging from about 2 to about 6 hours. Additional sodium bis(trimethylsilyl)amide and compound of formula (2) are then added and the reaction is stirred for an additional 8 to 24 hours to insure completion of the reaction. The reaction is then cooled to room temperature. The solvent is removed and the pentafluoro-alkylsulfanyl compound of formula (4) can be isolated and purified by techniques well known in the art, such as extraction, evaporation, trituration, chromatography, and recrystallization.

In Scheme A, step 2, the pentafluoro-alkylsulfanyl compound of formula (4) is deprotected with a suitable deprotecting agent and optionally oxidized with a suitable oxidizing agent to prepare a compound of formula (I).

For example, where $R^1$ and/or $R^3$ is the preferred protecting group, benzyl, and particularly if selective deprotection is desired, the deprotective removal of the benzyl group(s) on the pentafluoro-alkylsulfanyl compound of formula (4) can be carried out in a non-reactive solvent in the presence of an equimolar or a slight excess of an amine base such as sodium bis(trimethylsilyl)amide, and a suitable catalyst such as palladium-on-carbon, which is preferred. Preferred solvents for this reaction include tetrahydrofuran or diethyl ether, with tetrahydrofuran. The reaction is conducted at an elevated temperature of from about from about 50° C. to about 70° C. and stirred for a period of time ranging from about 4 to about 24 hours.

In the case where $R^1$ and/or $R^3$ are methyl and non-selective deprotection is acceptable, the deprotective removal of the methyl groups can be carried out either by the use of an alkali metal ethanethiolate (see G. I. Fetruell, et al., *Tetrahedron Letters*, 1327 (1970); idem. *Aust. J. Chem.*, 25: 1719 (1972) and A. S. Kende, et al., *Tetrahedron Letters*, 22: 1779 (1981) or by the use of either boron tribromide in methylene chloride at a temperature of between about −80° C. to 20° C. for a period of 6-12 hours (J. F. W. McOmie, et al., *Org. Syn., Coll. Volume V*, 412 (1973)) or $BBr_3.S(CH_3)_2$ in ethylene chloride at a temperature of about 80° C. to 85° C. (P. G. Williard, et al., *Tetrahedron Letters*, 21: 3731 (1981)).

Additionally, in order to prepare compounds of formula (I) where n is 1, a compound of formula (I) where n is 0 is further oxidized with a suitable oxidizing agent to provide a corresponding compound of formula (I) where n is 1. For example, a compound of formula (I) where n is 0 is dissolved in an alkanolic solvent such as methanol and contacted with a slight molar excess of a suitable oxidizing agent such as sodium periodate, which is preferred. The reaction carried out at room temperature for a period of time ranging from about 6 to about 24 hours.

A compound of formula (I) may be isolated and purified by techniques well known in the art, such as extraction, evaporation, trituration, chromatography, and recrystallization.

A general synthetic scheme for preparing compounds of formula (2) is set forth in Scheme B, wherein all substituents, unless otherwise indicated, are previously defined.

SCHEME B

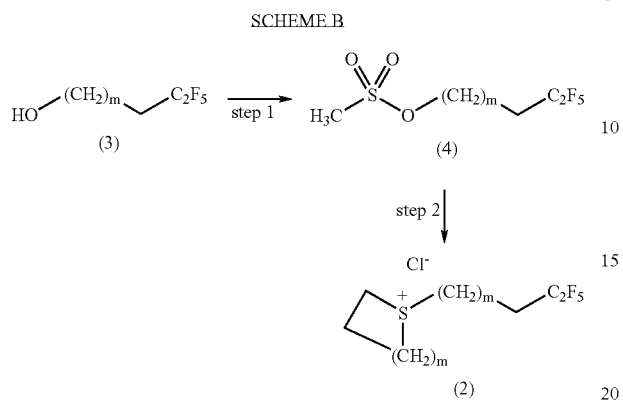

In Scheme B, step 1, a pentafluroalkylsulfonic ester of formula (4) is prepared by contacting a pentafluroalkanol of formula (3) with methanesulfonyl chloride.

For example, a pentafluoroalkanol of formula (3) is dissolved in a non-reactive organic solvent, such as dichloromethane, and cooled to a temperature of about 0° C. About 3 to about 6 molar equivalents of an amine base, preferably triethylamine, is added to the solution followed by the addition of a slight molar excess of methanesulfonyl chloride. The solution is stirred for a brief period of time, ranging from 30 minutes to 2 hours and then poured into 0.5 N HCl and washed with subsequent 0.5 N HCl. The pentafluroalkylsulfonic ester of formula (4) can be isolated and purified by techniques well known in the art, such as extraction, evaporation, trituration, chromatography, and recrystallization.

Appropriate pentafluoroalkanols of formula (3) are commercially available through Fluorochem or can be prepared as set forth analogously in Tetrahedron Letters 35, 9141-9144 (1994), the disclosure of which is hereby incorporated by reference.

In Scheme B, step 2, the pentafluoro-alkyl-tetrahydrothiophenium chloride of formula (2) is prepared by reacting the pentafluoroalkylester of formula (4) with tetrahydrothiophene. For example, the pentafluoroalkylester of formula (4) is reacted with about 2 to about 5 molar equivalents of tetrahydrothiophene in a sealed container or tube. The reaction is then heated to a temperature of about 100° C. and stirred for a period of time ranging from about 6 to about 24 hours. The solution is then cooled to room temperature and a small amount of an alkanol, preferably methanol, is added. The pentafluoro-alkyl-tetrahydrothiophenium chloride of formula (2) can be isolated and purified by techniques well known in the art, such as extraction, evaporation, trituration, chromatography, and recrystallization.

Compounds of formula (3) may be made according to procedures well known in the art. For example, preparative syntheses of compounds of formula (3) are taught by U.S. Pat. No. 5,929,090, U.S. Pat. No. 6,002,053, and Tetrahedron Letters 35, 9141-9144 (1994). Compounds of formula (3) wherein $X^1$ is —$NR^2$— may be prepared analogously according by C. R. Schmidt et al., *Bioorg. Med. Chem. Lett.* 9 (1999) 523-528. All of the patents and references set forth immediately above are incorporated by reference.

General Experimental Details

All solvents were ACS grade and were used as supplied. All reagents were commercially available and used without further purification unless otherwise noted. LCMS data was recorded on a Hewlett Packard 1100 series instrument. The method used was 5% acetonitrile—95% water (0.05% TFA) to 95% acetonitrile—5% water (0.05% TFA) over two minutes and hold for three minutes on a Waters Symmetry C18 2.1×50 mm column at 35° C. $^1$H NMR spectra were recorded at 400 MHz on a Varian Mercury VX 400 spectrometer unless otherwise noted.

Preparation 1

Methanesulfonic acid 4,4,5,5,5-pentafluoro-pentylester

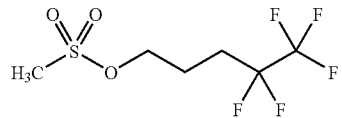

Dissolve 4,4,5,5,5-pentafluoropentanol (8.27 g, 46.42 mmol) in $CH_2Cl_2$ (100 mL) and cooled the solution to 0° C. Add triethylamine (20.00 mL, 143.49 mmol), followed by the drop wise addition of methanesulfonyl chloride (4.40 mL, 56.84 mmol). Stir the solution for 45 minutes, then pour into HCl (0.5 N, 100 mL). Wash the organic layer with HCl (0.5 N, 2×100 mL). Dry the organic layer ($Na_2SO_4$), filter, and concentrate in vacuo. Recovered 11.48 g (96%) of the desired methanesulfonic acid 4,4,5,5,5-pentafluoro-pentylester as a light yellow oil. $^1$H NMR (400 MHz, $CDCl_3$): δ 4.31 (t, J=6.0 Hz, 2H), 3.03 (s, 3H), 2.2 (m, 2H), 2.08 (m, 2H).

Preparation 2

1-(4,4,5,5,5-Petafluoro-pentyl)-tetrahydro-thiophenium; chloride

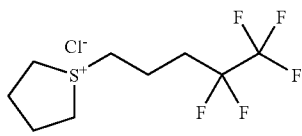

Dissolve methanesulfonic acid 4,4,5,5,5-pentafluoro-pentylester (6.25 g, 23.57 mmol) in tetrahydrothiophene (6.50 mL, 6.50 g, 73.72 mmol) in a sealed tube. Heat the solution to 100° C. and stir overnight. Cool the solution to room temperature and add MeOH (2 mL). Purify by ion exchange (SCX column washing with MeOH eluting with 1.0 M HCl in MeOH) to afford 4.47 g (64%) of the desired 1-(4,4,5,5,5-Petafluoro-pentyl)-tetrahydro-thiophenium; chloride as a light yellow oil. $^1$H NMR (400 MHz, $CDCl_3$): δ 3.6 (m, 2H), 3.47 (m, 2H), 3.31 (m, 2H), 2.22-2.47 (m, 6H), 2.12 (m, 2H). MS (ion spray): 249 (M-Cl).

Preparation 3

6-Benzyloxy-2-(4-methoxy-phenyl)-1-{4-[4-(4,4,5,5,5-pentafluoro-pentylsulfanyl)-butoxy]phenoxy}-naphtalene

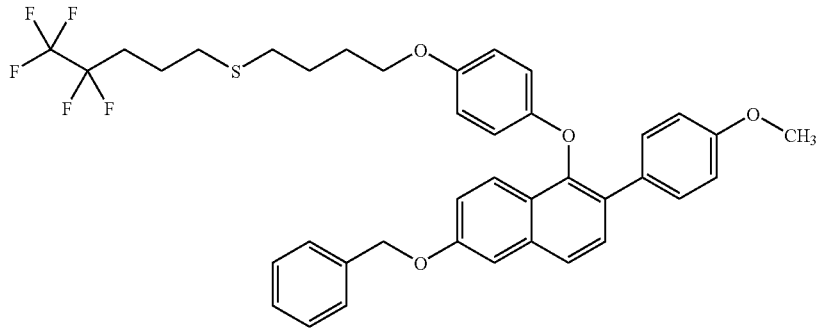

Dissolve 4-[6-Benzyloxy-2-(4-methoxy-phenyl)-naphthalen-1-yloxy]-phenol (0.465 g, 1.037 mmol) in THF (10 mL). Cool to 0° C. Add sodium bis(trimetylsilyl)amide (1.0 M in THF, 1.140 mL, 1.140 mmol). Add 1-(4,4,5,5,5-petafluoro-pentyl)-tetrahydro-thiophenium; chloride (0.2 M in THF, 5.700 mL, 1.140 mmol) to the solution and let warm to room temperature. Heat to 55° C. and stir for 4 hours. Add additional sodium bis(trimetylsilyl)amide (1.0 M in THF, 1.140 mL, 1.140 mmol), and petafluoro-pentyl)-tetrahydro-thiophenium; chloride (0.2 M in THF, 5.700 mL, 1.140 mmol) and stir overnight at 55° C. Cool to room temperature and concentrate in vacuo. Purify by column chromatography (eluting with 10% EtOAc in hexanes) to afford 0.610 g (84%) of the desired 6-Benzyloxy-2-(4-methoxy-phenyl)-1-{4-[4-(4,4,5,5,5-pentafluoro-pentylsulfanyl)-butoxy]phenoxy}-naphtalene as a white solid. $^1$H NMR (400 MHz, CDCl$_3$): δ 7.76 (d, J=9.3 Hz, 1H), 7.55 (d, J=8.3 Hz, 1H), 7.38 (m, 5H), 7.21-7.37 (m, 3H), 7.26 (m, 1H), 7.05 (dd, J=2.4, 9.3 Hz, 1H), 6.75 (m, 2H), 6.51 (m, 4H), 5.08 (s, 2H), 3.75 (t, J=14.2 Hz, 2H), 3.67 (s, 3H), 2.46 (m, 4H), 2.04 (m, 2H), 1.55-1.80 (m, 6H).

EXAMPLE 1

6-(4-Methoxy-phenyl)-5-{4-[4-(44,5,5,5-pentafluoro-pentylsulfanyl)-butoxy]-phenoxy}-naphthalen-2-ol

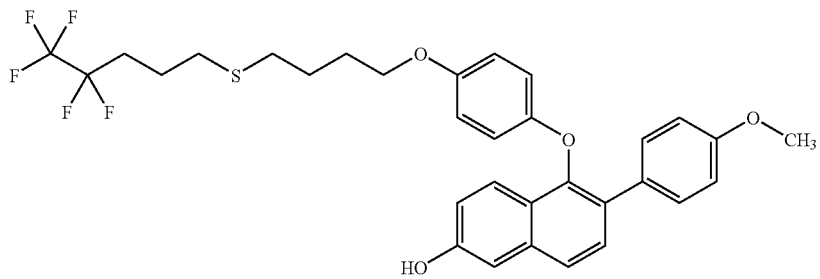

Add dry Pd/C (0.110 g, 0.104 mmol) to 6-benzyloxy-2-(4-methoxy-phenyl)-1-{4-[4-(4,4,5,5,5-pentafluoro-pentylsulfanyl)-butoxy]phenoxy}-naphtalene (0.590 g, 0.847 mmol). Add EtOH (25 mL), followed by ammonium formate (0.382 g, 6.058 mmol). Heat to reflux and stirred for 1.5 hours. Cool to room temperature and add additional Pd/C (0.610 g, 0.547 mmol), and ammonium formate (0.385 g, 6.105 mmol). Heat to reflux and stirred for 3 hours. Add celite (10 g) and filter washing with CH$_2$Cl$_2$ and CH$_3$OH. Concentrate the solution in vacuo. Dissolve the resulting residue in CH$_2$Cl$_2$ (20 mL) and wash the solution with H$_2$O (2×15 mL). Separate the layers and dry the organic (Na$_2$SO$_4$), filter and concentrate in vacuo. Purify by radial chromatography (eluting with 30% EtOAc in hexanes) to afford 0.318 g (62%) of the desired 6-(4-methoxy-phenyl)-5-{4-[4-(4,4,5,5,5-pentafluoro-pentylsulfanyl)-butoxy]-phenoxy}-naphthalen-2-ol as a white solid. $^1$H NMR (400 MHz, CDCl$_3$): δ 7.83 (t, J=9.3 Hz, 1H), 7.58 (d, J=8.3 Hz, 1H), 7.47 (m, 3H), 7.16 (d, J=2.4 Hz, 1H), 7.0 (m, 1H), 6.83 (dd, J=2.0, 6.8 Hz, 2H), 6.58 (m, 4H), 3.81 (t, J=5.9 Hz, 2H), 3.76 (s, 3H), 2.65-2.75 (m, 2H), 2.54 (m, 2H), 2.06-2.29 (m, 3H), 1.68-1.93 (m, 5H).

EXAMPLE 2

6-(4-Methoxy-phenyl)-5-{4-[4-(4,4,5,5,5-pentafluoro-pentane-sulfinyl)-butoxy]-phenoxy}-naphthalen-2-ol

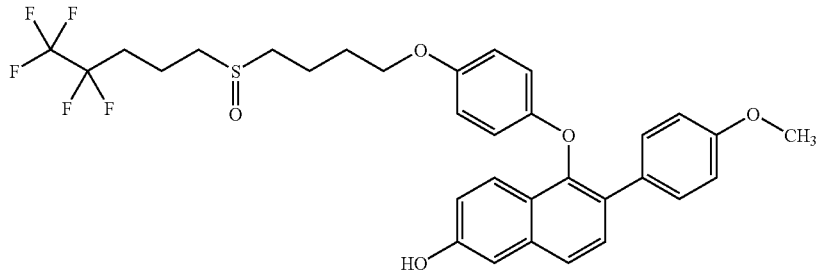

Dissolve 6-(4-methoxy-phenyl)-5-{4-[4-(4,4,5,5,5-pentafluoro-pentylsulfanyl)-butoxy]-phenoxy}-naphthalen-2-ol (0.313 g, 0.516 mmol) in MeOH (15 mL). Add sodium periodate (0.122 g, 0.570 mmol) in $H_2O$ (2 mL). Stir overnight at room temperature. Extract with EtOAc (30 mL). Wash with $H_2O$ (15 mL), $NaHCO_3$ (saturated solution, 15 mL), brine (20 mL). Dry the organics ($Na_2SO_4$), filter and concentrate in vacuo. Purify by radial chromatography (eluting with 50% EtOAc, 48% Hexanes, 2% MeOH) to afford 0.185 mg (58%) of the desired 6-(4-Methoxy-phenyl)-5-{4-[4-(4,4,5,5,5-pentafluoro-pentane-sulfinyl)-butoxy]-phenoxy}-naphthalen-2-ol as a white solid. $^1H$ NMR (400 MHz, $CDCl_3$): δ 7.79 (d, J=8.8 Hz, 1H), 7.55 (d, J=8.3 Hz, 1H), 7.47 (m, 3H), 7.19 (m, 1H), 7.02 (m, 1H), 6.82 (d, J=8:8 Hz, 2H), 6.57 (s, 4H), 3.76 (m, 5H), 2.65-2.84 (m, 4H), 2.10-2.25 (m, 4H), 1.79-1.93 (m, 4H). MS (ion spray): ES+: 623 (M+1); ES−: 621 (M−1).

Biological Test Procedure

General Preparation Procedure

Competition binding assay is run in a buffer containing 50 mM Hepes, pH 7.5, 1.5 mM EDTA, 150 mM NaCl, 10% glycerol, 1 mg/ml ovalbumin and 5 mM DTT, using 0.025 µCi per well $^3H$-Estradiol(NEN #NET517 at 118 Ci/ml, 1 mCi/ml), 10 ng/well ERAlpha or ERbeta receptor (PanVera). Competing compounds are added at 10 different concentrations. Non-specific binding is determined in the presence of 1 µM of 17-B Estradiol. The binding reaction (140 µl) is incubated for 4 hours at room temperature, then 70 µl of cold DCC buffer is added to each reaction (DCC buffer contains per 50 ml of assay buffer, 0.75 g of charcoal (Sigma) and 0.25 g of dextran (Pharmacia)). Plates are mixed 8 minutes on an orbital shaker at 4° C. Plates are then centrifuged at 3,000 rpm at 4° C. for 10 minutes. An aliquot of 120 µl of the mix is transferred to another 96-well, white flat bottom plate (Costar) and 175 µl of Wallac Optiphase "Hisafe 3" scintillation fluid is added to each well. Plates are sealed and shaken vigorously on an orbital shaker. After an incubation of 2.5 hrs, read plates in a Wallac Microbeta counter. The data is used to calculate an IC50 and % Inhibition at 10 µM. The $K_d$ for $^3H$-Estradiol is determined by saturation binding to ER alpha and ER beta receptors. The $IC_{50}$ values for compounds are converted to K; using Cheng-Prusoff equation and the $K_d$ determined by saturation binding assay.

Ishikawa human endometrial tumor cells are maintained in MEM (minimum essential medium, with Earle's salts and L-Glutamine, Gibco BRL, Gaithersburg, Md.), supplemented with 10% fetal bovine serum (FBS) (V/V), (Gibco BRL). One day prior to assay, growth media is changed to assay medium, DMEM/F-12 (3:1) (Dulbecco's Modified Eagle Medium: Nutrient Mixture F-12, 3:1 Mixture, phenol red-free, Gibco BRL) supplemented with 5% dextran coated charcoal stripped fetal bovine serum (DCC-FBS) (Hyclone, Logen, UT), L-Glutamine (2 mM), MEM sodium pyruvate (1 mM), HEPES (N-[2-hydroxyethyl]piperazine-N'-[2-ethanesulfonic acid]2 mM) all from Gibco BRL). After an overnight incubation, ishikawa cells are rinsed with Dulbecco's Phosphate Buffered Saline (1×) (D-PBS) without $Ca^{+2}$ and $Mg^{+2}$ (Gibco BRL), and trypsinized by a 3 minute incubation with 0.25% Trypsin/EDTA, phenol red-free (Gibco BRL). Cells are resuspended in assay medium and adjusted to 250,000 cells/ml. Approximately 25,000 cells in a 100 ul media are added to flat-bottom 96 wells microculture plates (Costar 3596) and incubated at 37° C. in a 5% $CO_2$ humidified incubator for 24 hours. The next day, serial dilutions of compounds are prepared in assay medium (at 6 times the final concentration in the assay). The assay is run in dual mode, agonist and antagonist modes. For the agonist mode, plates receive 25 µl/well of assay medium followed by 25 µl/well of diluted compounds (at 6× the final concentrations). For the antagonist mode, plates receive 25/well of 6 nM $E_2$ (β-Estradiol, Sigma, St. Louis, Mo.) followed by 25 µl/well of diluted compounds (at 6× the final concentrations). After an additional 48-hour incubation at 37° C. in a 5% $CO_2$ humidified incubator, media is aspirated from wells and 100 µl fresh assay medium is added to each microculture. Serial dilutions of compounds are prepared and added to the cells as described above. After an additional 72 hour incubation at 37° C. in a 5% $CO_2$ humidified incubator, the assay is quenched by removing media and rinsing plates twice in Dulbecco's Phosphate Buffered Saline (1×) (D-PBS) (Gibco BRL). The plates are dried for 5 min and frozen at −70° C. for at least 1 hour. The plates are then removed from the freezer and allowed to thaw at room temperature. To each well, 100 µl of 1-Step™ PNPP (Pierce Chemical Company, Rockford, Ill.) is added. After a 20-minute incubation, plates are read on a spectophotometer at 405 nm. The data is fitted to a linear interpolation to derive EC50 (for agonist mode) or IC50 (for antagonist mode) values. For the agonist mode, a % efficacy for each compound is calculated versus the response to Tamoxifen. For the antagonist mode, a % efficacy for each compound is calculated versus E2 (1 nM) alone.

MCF-7 breast adenocarcinoma cells (ATCC HTB 22) are maintained in MEM (minimal essential medium, phenol red-free, Gibco BRL) supplemented with 10% fetal bovine serum (FBS) (V/V), L-glutamine (2 mM), sodium pyruvate (1 mM), HEPES ((N-[2-hydroxyethyl]piperazine-N'-[2-ethanesulfonic acid]10 mM}, non-essential amino acids (0.1 mM) and Penicillin Streptomycin(IX). Seven days prior to assay, MCF-7 cells are switched to assay media which is the same as maintenance medium except supplemented with 10% dextran-coated charcoal-stripped fetal bovine serum (DCC-FBS) assay medium in place of 10% FBS. MCF-7 cells are removed from flasks using 10× Trypsin EDTA (phenol red free, Gibco BRL) and diluted to 1× in (Ca++/Mg++ free HBSS (phenol red-free). Cells are adjusted to 80,000 cells/ml in assay medium. Approximately 8,000 cells (100 µl) are added to each well in 96 well Cytostar T scintillation plates (Amersham) and incubated at 37° C. in a 5% $CO_2$ humidified incubator for 24 hours to allow cell adherence and equilibration after transfer. Serial dilutions of drugs are prepared in assay medium at 4× the final desired concentration). A 50 µl aliquot of drug dilutions (at 4× the final assay concentration) is transferred to duplicate wells followed by 50 µl assay medium for the agonist mode or 50 µl of 40 pM of E2 for the antagonist mode to a final volume of 200 µl. For each of the agonist plates, a basal level (media), and a maximum stimulated level (with 1 µM E2) is determined. For each of the antagonist plates, a basal level (media) and a E2 (10 pM) alone control is determined. After an additional 48 hours at 37° C. in a 5% $CO_2$ humidified incubator, 20 µl of assay medium containing 0.01 µCi of $^{14}$C-thymidine (52 mCi/mmol, 50 µCi/ul, Amersham) is added to each well. The plates are incubated overnight in the same incubator and then counted on the Wallac Microbeta counter. The data is averaged to calculate an IC50 and % inhibition @ 1 µM for the antagonist mode. For the agonist mode, an EC50 and percent of maximum E2 stimulation and concentration of maximum stimulation is calculated. The following Table provides data for the compound 6-(4-methoxy-phenyl)-5-{4-[4-(4,4,5,5,5-pentafluoro-pentane-sulfinyl)-butoxy]-phenoxy}-naphthalen-2-ol from Example 2.

TABLE

| Binding | | MCF-7 | | Ishikawa | |
|---|---|---|---|---|---|
| ER a Ki (nM) | ER b Ki (nM) | IC 50 (nM) | Antag. % Eff. | IC 50 (nM) | Antag. % Eff. |
| 0.3 | 0.2 | 2.5 | 86 | 6.8 | 100 |

Uterine Eosinophil Peroxidase (EPO) Assay

The uteri from above are kept at 4° C. until time of enzymatic analysis. The uteri are then homogenized in 50 volumes of 50 mM Tris buffer (pH –8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Prevention of Breast Cancer

This invention also relates to the administration of a compound of formula (I) to a recipient who is at risk of developing de novo breast cancer. The term "de novo", as used herein, means the lack of transformation or metamorphosis of normal breast cells to cancerous or malignant cells in the first instance. Such a transformation may occur in stages in the same or daughter cells via an evolutionary process or may occur in a single, pivotal event. This de novo process is in contrast to the metastasis, colonization, or spreading of already transformed or malignant cells from the primary tumor site to new locations.

A person who is at no particular risk of developing breast cancer is one who may develop de novo breast cancer, has no evidence or suspicion of the potential of the disease above normal risk, and who has never had a diagnosis of having the disease. The greatest risk factor contributing to the development of breast carcinoma is a personal history of suffering from the disease, or an earlier occurrence of the disease, even if it is in remission with no evidence of its presence. Another risk factor is family history of the disease.

Induction of mammary tumors in rats by administration of the carcinogen N-nitroso-N-methylurea is a well-accepted animal model for the study of breast cancer and has been found suitable for analyzing the effect of chemopreventive agents.

In two separate studies, 55-day old female Sprague-Dawley rats are given an intravenous (Study 1) or intraperitoneal (Study 2) dose of 50 mg of N-nitroso-N-methylurea per kilogram of body weight one week prior to feeding ad libitum a diet into which varying amounts of F-I, (Z)-2-[4-(1,2-diphenyl-1-butenyl)phenoxy]-N,N-dimethylethanamine base (tamoxifen base), or control are blended.

In Study 1, the dietary doses of 60 mg/kg of diet and 20 mg/kg of diet translates into roughly comparable doses of 3 and 1 mg/kg of body weight for the test animals.

In Study 2, the dietary doses of 20, 6, 2, and 0.6 mg/kg of diet translates roughly into comparable doses of 1, 0.3, 0.1 and 0.03 mg/kg of body weight for the test animals.

Rats are observed for evidence of toxicity and are weighed and palpated for tumor formation once a week. The animals are sacrificed after thirteen weeks (Study 1) or eighteen weeks (Study 2) and tumors are confirmed and weighed at autopsy.

Therapeutic Methods of Use and Dosages

The present invention also provides a method of treatment or prevention of disease conditions associated with an aberrant physiological response to endogenous estrogen including breast cancer and endometrial cancer.

As used herein, the term "patient" refers to a warm-blooded animal or mammal which is in need of inhibiting a disease associated with estrogen deprivation or in need of inhibiting a disease associated with an aberrant physiological response to endogenous estrogen. It is understood that guinea pigs, dogs, cats, rats, mice, hamsters, and primates, including humans, are examples of patients within the scope of the meaning of the term. Preferred patients include humans. Most preferred patients include postmenopausal female humans.

As used herein, the term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

One example of a pathological condition associated with abnormal cellular responses to endogenous estrogen in tissues is estrogen dependent breast cancer. Estrogen dependent breast tumor cells proliferate in the presence of estrogen and the treatment of this disease has been to stop all action of estrogen on these cells.

As used herein, the term "therapeutically effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose for human use will contain a nontoxic dosage level of from about 1 mg to about 600 mg/day of a compound of the present invention. Preferred daily doses generally will be from about 1 mg to about 1000 mg/day. Most preferred doses range may range from 20 mg to about 100 mg, administered once to three times per day.

The compounds of this invention can be administered by a variety of routes including oral, rectal, transdermal, subcutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Compounds of formula I, alone or in combination with a pharmaceutical agent of the present invention, generally will be administered in a convenient formulation.

We claim:

1. A compound 6-(4-Methoxy-phenyl)-5-{4-[4-(4,4,5,5,5-pentafluoro-pentylsulfanyl)-butoxy]-phenoxy}-naphthalen-2-ol; or a pharmaceutically acceptable salt thereof.

2. A compound 6-(4-Methoxy-phenyl)-5-{4-[4-(4,4,5,5,5-pentafluoro-pentane-sulfinyl)-butoxy]-phenoxy}-naphthalen-2-ol; or a pharmaceutical acceptable salt thereof.

3. A pharmaceutical composition comprising a therapeutically effective amount of a compound according to claim 1, in combination with a pharmaceutically acceptable carrier, diluent, or excipient.

4. A pharmaceutical composition comprising a therapeutically effective amount of a compound according to claim 2 in combination with a pharmaceutically acceptable carrier, diluent, or excipient.

* * * * *